United States Patent [19]

Urdea

[11] Patent Number: 5,656,731
[45] Date of Patent: Aug. 12, 1997

[54] NUCLEIC ACID-AMPLIFIED IMMUNOASSAY PROBES

[75] Inventor: Michael S. Urdea, Alamo, Calif.

[73] Assignee: Chiron Corporation, Emeryville, Calif.

[21] Appl. No.: 85,681

[22] Filed: Jul. 1, 1993

Related U.S. Application Data

[63] Continuation of Ser. No. 519,212, May 4, 1990, abandoned, which is a continuation-in-part of Ser. No. 463,022, Jan. 10, 1990, abandoned, and a continuation-in-part of Ser. No. 340,031, Apr. 18, 1989, Pat. No. 5,124,246, which is a continuation-in-part of Ser. No. 252,638, Sep. 30, 1988, abandoned, which is a continuation-in-part of Ser. No. 185,201, Apr. 22, 1988, abandoned, which is a continuation-in-part of Ser. No. 109,282, Oct. 15, 1987, abandoned.

[51] Int. Cl.$^6$ ................................................. C07K 16/00
[52] U.S. Cl. ................ 530/391.1; 435/6; 435/7.1; 435/7.7; 435/7.72; 435/91.1; 435/810; 436/501; 530/387.1; 530/391.3; 530/391.5; 536/23.1; 536/24.1; 536/24.31; 536/24.32; 536/24.33; 935/77; 935/78
[58] Field of Search .................... 435/7.1, 6, 91, 435/810, 7.7, 91.1; 436/501; 536/22.1, 23.1, 24.31–24.33, 24.1; 935/77, 78; 530/387.1, 391.1, 391.3, 391.5

[56] References Cited

U.S. PATENT DOCUMENTS

| | | | |
|---|---|---|---|
| 4,299,916 | 11/1981 | Litman et al. | 435/6 |
| 4,563,419 | 1/1986 | Ranki et al. | 435/6 |
| 4,626,501 | 12/1986 | Landes | 435/6 |
| 4,687,732 | 8/1987 | Ward et al. | 435/6 |
| 4,692,509 | 9/1987 | Dattagupta | 530/303 |
| 4,737,454 | 4/1988 | Dattagupta et al. | 435/6 |
| 4,749,647 | 6/1988 | Thomas et al. | 435/6 |
| 4,766,072 | 8/1988 | Jendrisak et al. | 435/91 |
| 4,828,979 | 5/1989 | Klevan et al. | 435/6 |
| 4,868,105 | 9/1989 | Urdea et al. | 435/6 |
| 4,873,187 | 10/1989 | Taub | 435/5 |

(List continued on next page.)

FOREIGN PATENT DOCUMENTS

| | | |
|---|---|---|
| 0154884 | 9/1985 | European Pat. Off. . |
| 0225807 | 6/1987 | European Pat. Off. . |
| 0317077 | 5/1989 | European Pat. Off. . |
| 2125964 | 3/1984 | United Kingdom . |
| WO 87/06270 | 10/1987 | WIPO . |
| WO 89/04375 | 5/1989 | WIPO . |
| 8903891 | 5/1989 | WIPO . |
| WO 90/02819 | 3/1990 | WIPO . |

OTHER PUBLICATIONS

Dunn et al. (1983) J. Mol. Biol., vol. 166, pp. 477–535.
Czichos et al. (1989) Nuc. Acids Res., vol. 17, No. 4, pp. 1563–1572.
Fahrlander et al., "Amplifying DNA probe signals: a 'Christmas tree' approach" *Bio/Technology* (1988) 6:1165–1168.
Ziemer et al., "Sequence of Hepatitis B virus DNA incorporated into the genome of human hepatoma cell line" *Virology* (1985) 53(3):885–892.
Chu et al., *Nucleic Acids Research* (1986) 14(14):5591–5603.
Syvanen et al., *Nucleic Acids Research* (1986) 14(12):5037–5048.
Syvanen et al., *Nucleic Acids Research* (1988) 16(23):11327–1133.

*Primary Examiner*—George C. Elliott
*Assistant Examiner*—Ardin H. Marschel
*Attorney, Agent, or Firm*—Tyler Dylan, Ph.D.; Kenneth M. Goldman; Robert P. Blackburn

[57] ABSTRACT

In one aspect of this invention, various protein/nucleic acid hybrid probes are described which can be used to amplify the detectable signal in immunoassays. The protein moiety is capable of functioning either as an antibody or an antigen. The nucleic acid moiety serves as a signal amplifier. In another aspect, various methods of amplifying the detectable signal in immunoassays by use of the hybrid probes and related polynucleotide probes are disclosed.

31 Claims, 7 Drawing Sheets

U.S. PATENT DOCUMENTS

| | | | |
|---|---|---|---|
| 4,882,269 | 11/1989 | Schneider et al. | 435/6 |
| 4,910,300 | 3/1990 | Urdea et al. | 536/287 |
| 4,925,785 | 5/1990 | Wang et al. | 435/6 |
| 4,957,858 | 9/1990 | Chu et al. | 435/6 |
| 5,124,246 | 6/1992 | Urdea et al. | 435/6 |
| 5,175,270 | 12/1992 | Nilsen et al. | 536/27 |
| 5,428,132 | 6/1995 | Hirsch et al. | 530/387.1 |
| 5,571,670 | 11/1996 | Urdea et al. | 435/6 |

FIG. 1-1
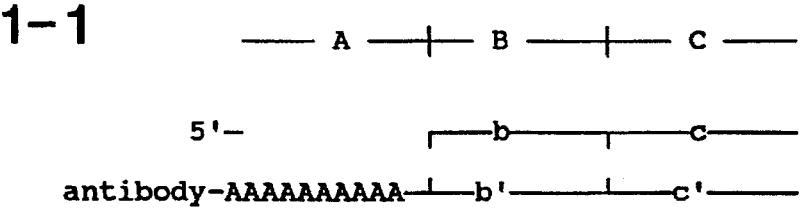
FIG. 1-2
```
   <    A    >              <      B     (T7 PROMOTER)       >
         5'-TTTTTTTTTCTGGCTTATCGAAATTAATACGACTCACTATA...
ANTIBODY -3'-AAAAAAAAAGACCGAATAGCTTTAATTATGCTGAGTGATAT...
          <      C      (TRANSCRIBED REGION)   >
   ...GGGAGATGTGGTTGTCGTACTTAGCGAAATACTGTCCGAGTCG
   ...CCCTCTACACCAACAGCATGAATCGCTTTATGACAGGCTCAGC
                      template strand
```
FIG. 1-3
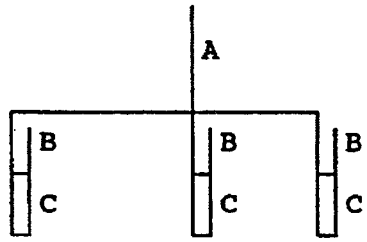
FIG. 1-4
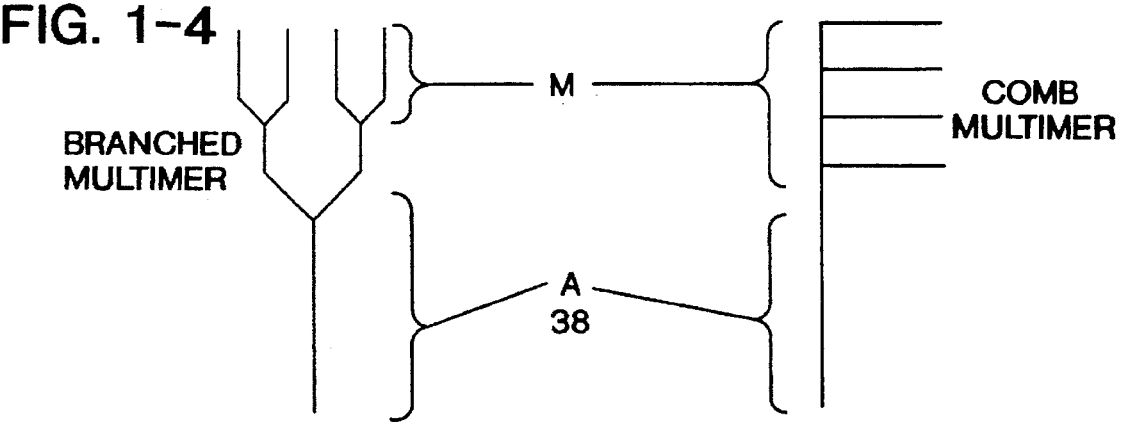

FIG. 4-1
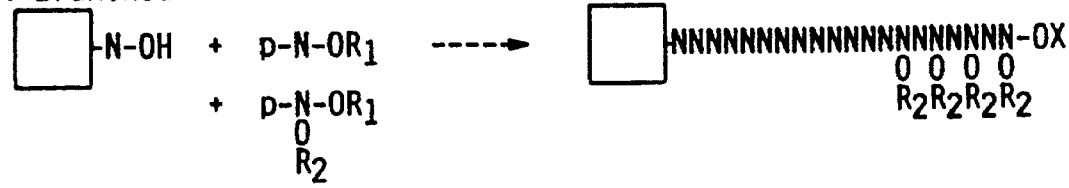
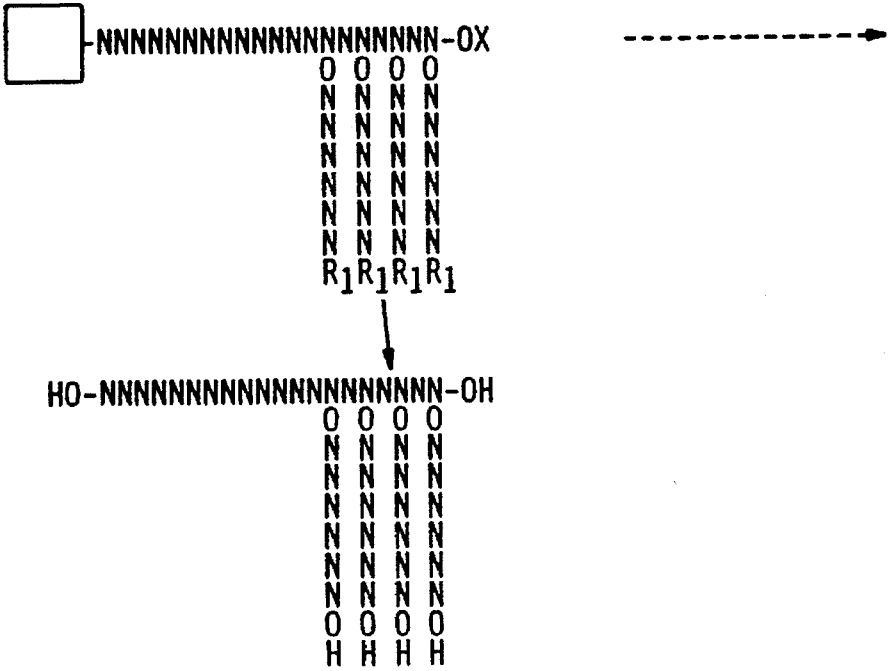

NUCLEIC ACID-AMPLIFIED IMMUNOASSAY PROBES

This application is a file-wrapper-continuation of U.S. patent application Ser. No. 07/519,212, filed 04 May 1990, now abandoned, which was a continuation-in-part of U.S. patent application Ser. No. 07/463,022, filed 10 Jan. 1990, now abandoned, and of U.S. patent application Ser. No. 07/340,031, filed 18 Apr. 1989, which issued as U.S. Pat. No. 5,124,246 on 23 Jun. 1992, which was a continuation-in-part of U.S. patent application Ser. No. 07/252,638, filed 30 Sep. 1988, now abandoned, which was a continuation-in-part of U.S. patent application Ser. No. 07/185,201, filed 22 Apr. 1988, now abandoned, which was a continuation-in-part of U.S. patent application Ser. No. 07/109,282, filed 15 Oct. 1987, now abandoned. Additionally, an international application, PCT/US88/03664, was filed on 14 Oct. 1988, based on U.S. applications Ser. Nos. 07/252,638, 07/185,201 and 07/109,282, and was published 5 May 1989 (Int. Pub. No. WO89/03891). The disclosures of all these related applications are incorporated herein by reference.

DESCRIPTION

1. Technical Field

This invention relates generally to the fields of immunology and nucleic acid chemistry. More specifically, it relates to the use of nucleic acid hybridization as a means of amplifying the detectable signal in immunoassays.

2. Background Art

Nucleic acid hybridizations are now commonly used in genetic research, biomedical research and clinical diagnostics to detect and quantify particular nucleotide sequences which are present in heterogenous mixtures of DNA, RNA, and/or other materials. In the basic nucleic acid hybridization assay, single-stranded analyte nucleic acid (either DNA or RNA) is hybridized, directly or indirectly, to a labeled nucleic acid probe, and the duplexes containing label are quantified. Both radioactive and non-radioactive labels have been used.

The basic assay lacks sensitivity. When the analyte is present in low copy number or dilute concentration the signal cannot be distinguished from the background noise. Variations of the basic scheme have been developed to facilitate separation of the target duplexes from extraneous material and/or to amplify the analyte sequences in order to facilitate detection, but these variations have suffered generally from complex and time consuming procedures, high background, low sensitivity, and difficulty in quantification. For a general discussion of these variations see International Pub. No. 89/03891.

Immunoassays are also commonly used in genetic research, biomedical research and clinical diagnostics to detect and quantify particular antigenic epitopes which are present in heterogenous mixtures of blood samples, cellular extracts and other materials. A basic immunoassay involves the specific binding of an antibody, either monoclonal or polyclonal, to a target antigen and a means for detecting the reaction. Such means have been incorporated into various assays including direct, indirect and sandwich immunoassays. However, the sensitivity of detection of the essential antigen/antibody interaction has presented much the same problems as described above for nucleic acid hybridizations.

Various techniques such as radioimmunoassay, immunoperoxidase, and ELISA are presently used for immunoassays. However, radioimmunoassays have the disadvantage of requiring the use of dangerous and environmentally unsound reagents and immunoproxidase and ELISA suffer from a low signal to noise ratio and are limited in signal amplification.

A primary objective of the present invention is to provide signal amplification methods utilizing unique polynucleotide molecules, which has proved useful in nucleic acid hybridization assays, for use in immunoassays. These amplifier probes provide a highly reproducible gain in signal, a highly reproducible signal-to-noise ratio, are themselves quantifiable and reproducible, and are capable of combining specifically with an analyte antigen present at low concentration, and also with "universal" nucleic acid reporter moieties to form stable complexes.

Commonly owned U.S. Pat. No. 4,868,105, issued 19 Sep. 1989, the disclosure of which is hereby incorporated by reference, describes a solution phase hybridization sandwich assay in which the analyte nucleic acid is hybridized to a "labeling probe" and to a "capturing probe". The probe-analyte complex is coupled by hybridization to a solid-support. This permits the analyte oligonucleotide to be removed from solution as a solid phase complex, thereby concentrating the analyte, facilitating its separation from other reagents, and enhancing its subsequent detection.

Commonly owned co-pending U.S. application, Ser. No. 340,031, claims linear and branched multimeric polynucleotide probes which have two domains, and methods of use of these probes as signal amplifiers in nucleic acid hybridization assays. The first domain is complementary to a single-stranded oligonucleotide sequence of interest, and the second domain is comprised of a multiplicity of single-stranded oligonucleotide subunits that are complementary to a single-stranded labeled oligonucleotide.

Commonly owned co-pending U.S. application, Ser. No. 463,022, claims polynucleotide probes which have three domains, and methods of use of these probes as signal amplifiers in nucleic acid hybridization assays. The first domain is complementary to a single-stranded oligonucleotide sequence of interest, the second domain is capable of functioning as a promoter for a bacterial phage DNA-dependent RNA polymerase enzyme activity, and the third domain is capable of functioning as a transcriptional template for the polymerase activity.

Protein/DNA hybrid molecules have been used as probes in nucleic acid hybridization assays where the protein moiety functions as a labeling component (Czichos, J., et al, Nucl. Acids Res. (1989) 17:1563; U.S. Pat. No. 4,873,187; U.S. Pat. No. 4,737,454.

Protein/DNA hybrid molecules have also been used as probes in immunoassays. U.S. Pat. No. 4,692,509 describes a radioactively labeled hybrid probe comprising a protein and a covalently linked radioactive oligonucleotide. The radioactive moiety is used to indicate the presence of the protein moiety in a biological assay. E.P.A. No. 154 884 discloses a protein/DNA hybrid molecule in which the protein moiety specifically recognizes a target protein and the nucleic acid moiety provides a labeling function.

SUMMARY OF THE INVENTION

One aspect of the invention is a polypeptide/polynucleotide-hybrid molecular probe for use as an amplifier of the detectable signal in immunoassays. In one embodiment the "polymerase probe" comprises three domains:

(a) a first domain (A) which is a polypeptide and functions as an antibody specific for a known antigen;

(b) a second domain (B) which is a double-stranded polydeoxyribonucleotide capable of functioning as a promoter for a DNA-dependent RNA polymerase enzyme activity; and (c) a third domain (C) which is either single- or double-stranded and adjacent to the second domain, such that the third domain is capable of functioning as a template for the promoter activity of the second domain.

A second embodiment is a polypeptide/polynucleotide-hybrid molecular probe for use as an amplifier of the detectable signal in immunoassays. This "multimer probe" comprises two domains:

(a) a first domain (A) which is a polypeptide capable of functioning as an antibody which binds specifically to a known antigen;

(b) a second domain (M) comprising a multiplicity of single-stranded oligonucleotide subunits that are capable of binding specifically to a single-stranded nucleic acid sequence of interest; and (c) a means for conjugating the first and second domains.

Another aspect of the invention is a method of amplifying a detectable signal in an immunoassay by use of the polymerase probes described supra. This method comprises:

(a) immobilizing the antigenic analyte, directly or indirectly, on a solid substrate;

(b) directly or indirectly binding to the analyte a first molecular probe comprising:
   (i) a binding domain (A);
   (ii) a second domain (B) which is a double stranded DNA sequence capable of functioning as a promoter for a DNA-dependent RNA polymerase enzyme activity; and
   (iii) a third domain (C) which is either single- or double-stranded and adjacent to domain B, such that the third domain is capable of functioning as a template for the promoter activity of the second domain;

(c) removing the unbound probe;

(d) transcribing multiple copies of RNA oligomers which are complementary to the template sequence, c', of the third domain, C, of the probe construct via a DNA-dependent RNA polymerase activity; and (e) quantifying the transcripts.

Another aspect of the invention is another method of amplifying a detectable signal in an immunoassay by use of the multimer probes described supra. This method comprises:

(a) immobilizing the analyte, directly or indirectly on a solid substrate;

(b) directly or indirectly binding to the analyte a hybrid molecular probe comprising:
   (i) a binding domain (A) which is a polypeptide capable of functioning as an antibody which binds specifically to an antigen of interest; and
   (ii) a second domain (M) comprising a multiplicity of single-stranded DNA oligonucleotide subunits that are capable of binding specifically to a single-stranded labeled oligonucleotide; and
   (iii) a means for conjugating the first and second domains;

(c) removing unbound probe;

(d) hybridizing single-stranded labeled oligonucleotides which comprise a nucleotide sequence which is substantially complimentary to the subunit sequence of the domain M probe to the subunits of the second domain;

(e) removing unbound labeled oligonucleotide; and (f) quantifying the amount of labeled oligonucleotide bound to the probe.

Yet another embodiment is a method of amplifying a detectable signal in a competitive immunoassay which comprises:

(a) constructing a hybrid molecule in which domain A is a polypeptide capable of functioning as a hapten, and this domain is conjugated either to a B/C domain of the polymerase probe or a M domain of the multimer probe;

(b) immobilizing the hybrid molecule, directly or indirectly upon a solid substrate in the presence of a competing analyte;

(c) removing the unbound probe; and either (d) transcribing multiple copies of RNA oligomers via a DNA-dependent RNA polymerase activity and quantifying the transcripts—this in the instance that a polymerase probe is utilized; or (e) hybridizing single-stranded labeled oligonucleotides, to the subunits of the M domain, removing the unbound label and quantifying the bound label—this in the instance that a multimer probe is utilized.

BRIEF DESCRIPTION OF THE DRAWINGS

FIG. 1-1 is a schematic representation of a monomeric polymerase-type amplifier probe. Capital letters designate domains, and lower case letters-designate strands within a domain. A primed letter designates a lower strand (read 3'- to 5'-, left to right). The A domain is an antibody which recognizes a target epitope. The B domain is the promoter for a RNA polymerase. The c' sequence is the template for the RNA polymerase. The probe is synthesized as a single strand. The AAAAAAA at the end of the C region represents the poly-A linker added to allow for self-annealing. The A/T region between the A and B domain is optionally required to retain full antibody activity.

FIG. 1-2 is the DNA sequence of one embodiment of the polymerase-type amplifier probe. The promoter domain, B, consists of the consensus sequence of the bacteriophage T7 promoter (5'-TAATACGACTCACTATA-3') plus 15 additional residues 5' to the promoter sequence.

FIG. 1-3 is a schematic representation of a multimeric polymerase-type amplifier probe in which the A domain functions as an antibody and the double stranded B and C domains are self-annealing.

FIG. 1-4 is a schematic representation of multimeric amplifier probes in which the A domain functions as an antibody and the M domain is comprised of multiple oligomeric subunits. Both branched and comb-like multimers are depicted.

FIG. 2-1 is a schematic representation of a sandwich immunoassay system which incorporates the polymerase-type amplifier probe. The analyte protein is indirectly immobilized upon a solid substrate by complexing with a first antibody (e.g. a "rab" (rabbit)—antibody); and indirectly joined to the amplifier probe by complexing with a second antibody (e.g. a mouse antibody).

FIG. 2-2 is a schematic representation of a sandwich hybridization/immunoassay system. The analyte protein is indirectly immobilized as above. The second antibody (mouse-anti-analyte) is complexed with a hybrid antibody/polynucleotide molecule in which the protein moiety functions as an anti-mouse antibody and the polynucleotide moiety is complementary to the a' nucleotide region of the amplifier probe (in this case, a multimer probe).

FIG. 3 depicts the use of RNA polymerase transcripts as reporter molecules in an immunoassay. After the sandwich complex which incorporates the polymerase probe is formed, RNA polymerase is added and multiple RNA transcripts (c) complementary to the template sequence (c') are produced. These sequences have two sub-domains: c1 which is complementary to a capture probe, immobilized upon a solid substrate; and c2 which is complementary to a labelling probe. This allows for indirect immobilization of the label and easy quantification of the hybridization assay signal. "*" designates the incorporated label which may be radioactive, chemiluminescent, fluorescent or enzymatic.

FIGS. 4-1 through 4-5 illustrate procedures used in making multimers having "comb-like" and/or bifurcated structures.

DETAILED DESCRIPTION OF THE INVENTION

Definitions

Figures 1, 2:
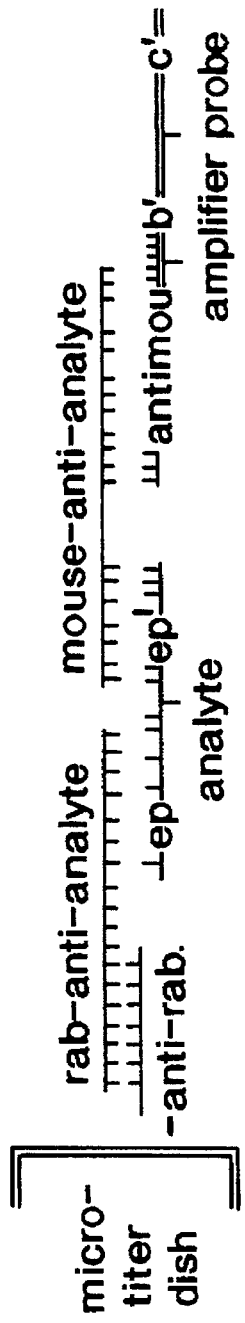
Figure 2:
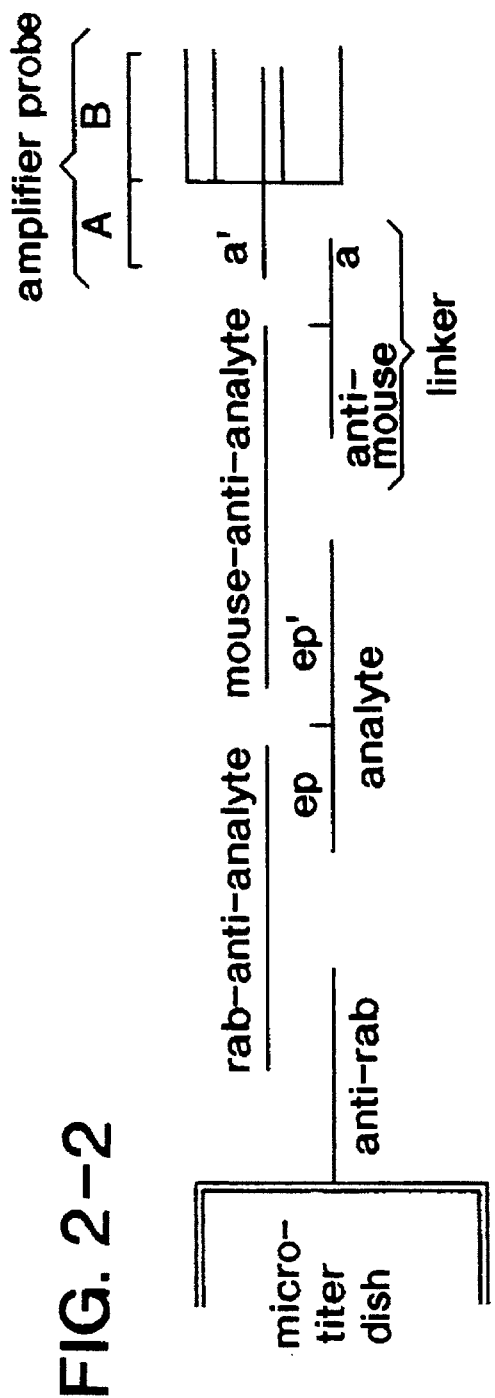

A "detectable signal" is a transmissible indicium of the occurrence of a biochemical event such as a nucleic acid hybridization or the binding of an antigen and antibody. The subject application describes methods of amplifying the detectable signal of immunoassays.

"DNA-dependent RNA polymerase" is an enzyme which facilitates the polymerization of RNA of specific sequence from a complementary DNA template.

A "domain" is a particular region of a biochemical molecule characterized by its function.

An "epitope" is that portion of an immunogenic molecule that is specifically recognized by, and complexes with, its corresponding antibody in an immunological reaction.

A nucleotide/peptide "hybrid" molecule comprise both nucleic acid residues and amino acid residues, each in a separate functional domain of the molecule.

An "immunogen" is a substance which can react in a specific fashion with an antibody.

An "immunological reaction" is the specific recognition and binding of an antibody to the epitope of an immunogen. An "immunoassay" is a method of determining the presence of an epitope by combining an immunological reaction with a means for detecting and quantifying the reaction.

A "polydeoxyribonucleotide" is a polymeric DNA molecule. A "polynucleotide" is a polymeric DNA or RNA molecule.

A "promoter" is the site on a polydeoxyribonucleotide to which a RNA polymerase enzyme binds preparatory to initiating transcription.

"RNA-dependent RNA polymerase" is an enzyme which facilitates the polymerization of RNA of specific sequence from a complementary RNA template.

"Transcription" is an process, mediated by an enzyme, by which RNA is formed from a complementary polynucleotide template.

The "upper strand" of a double-stranded DNA molecule is the strand whose 5'-end is on the left as the sequence is read from left to right. The sequence of this strand is always presented above the sequence for its complementary "lower strand" which is read 3'- to 5'-, left to right.

Modes for Carrying Out the Invention
I—Amplification Probes
A—Polymerase Probes

One aspect of this invention is a DNA amplification probe (referred to as a "polymerase probe") containing three functional domains. This probe is used to enhance the detectable signal in immunoassays.

The first domain (A—FIG. 1-1) is a polypeptide which functions as an antibody with specificity for an antigen of choice. The functional region of the polypeptide is followed by a region of either amino acid or nucleic acid residues, i.e.—a spacer region, which does not substantially interfere with the activity of the antibody. The antibody activity can be specific for an epitope of the analyte itself; however, in a preferred embodiment, the antibody is directed to an antigenic determinant of the particular immunoglobin used in the assay described infra (e.g. anti-rabbit IgG, or anti-human IgG—See FIG. 2-1). As applied, the analyte is contacted with a specific antibody, excess antibody is removed and the amplification probe is then allowed to react with the bound antibody.

Preferably, the analyte is first immobilized upon a solid substrate to facilitate subsequent washing procedures. This immobilization may be direct (e.g.—biological preparations containing the analyte might be bound to a nitrocellulose filter) or indirect (e.g.—a specific antibody might be immobilized on a solid substrate and the analyte subsequently bound to the immobilized antibody).

The second domain (B—FIG. 1-1), usually 10 to 40 base pairs in length, preferably 20 to 35 base pairs, more preferably 30 to 35 base pairs, is double stranded and functions as a DNA-directed RNA polymerase promoter. This promoter is usually derived from the promoter sequence of a bacterial phage, preferably any of the phage T3, T7, or SP6, more preferably from bacteriophage T7. This class of RNA polymerases is highly promoter specific. The T7 promoter is probably the best characterized (FIG. 1-1). DNA sequences from 17 T7 promoters are known and a consensus sequence had been deduced: 5'-TAATACGACTCACTATA-3' (Oakley and Coleman, *Proc. Nat. Acad. Sci.* (1977) 74:4266; Dunn and Studier, *J. Molec. Biol.* (1983) 166:477). Sequences 3' to the promoter on the complementary strand (the c' segment, whose 3' end is adjacent to the 5' end of the b' segment) serve as the template for transcription and the transcription of many template sequence variations can be accommodated (FIG. 1-1). Only the promoter region itself must be double-stranded (Milligan et al, *Nuc. Acids Res.* (1987) 15:8783).

Extensions at the 5' end of the promoter have little effect on transcription. For example, in a preferred embodiment, the B region consists of the consensus sequence of the T7 promoter plus additional bases 5' to the consensus sequence which are identical to the sequence of the pT7 plasmids (available from US Biochemicals) up to the Pvu II restriction site (FIG. 1-1). These sequences may or may not be extraneous.

The third domain (C—FIG. 1-1) is directly 3' to the second domain and the c' strand of this domain serves as the template for the domain B promoter. Domain C is usually 30 to 80 nucleotides in length, preferably 35 to 50 nucleotides, most preferably 40 to 45 nucleotides. This domain may be either single or double stranded The 3' end of the c' template strand (directly adjacent to the promoter) usually is a cytosine residue and consequently, the 5' end of the upper strand is usually a guanosine residue.

Figure 3:
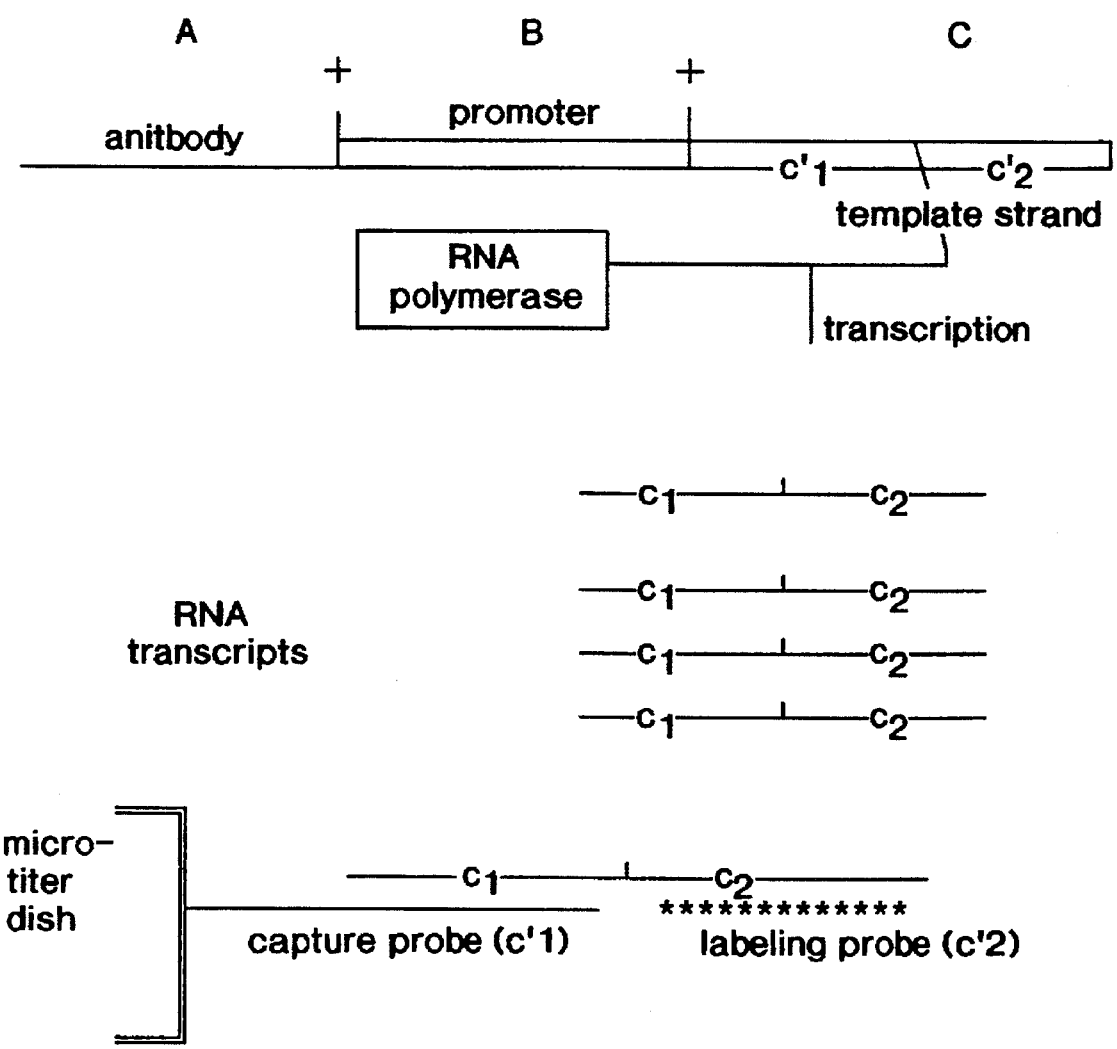

The RNA transcription product (c) of the C domain functions as a reporter molecule for the presence and quantity of analyte (FIG. 3). Signal amplification occurs because each template produces $10^1$ to $10^4$ transcripts. The sequence of this domain is designed with a random sequence, evaluated by computer analysis to minimize the possibility of cross-reaction with other probes in the system.

The sequence of the C domain is designed for a specific detection scheme and several such schemes may be employed to quantify the transcripts. For example, the transcription product (c) of the C domain may be subdivided into 2 subdomains—$c_1$ and $c_2$ (FIG. 3). Subdomain $c_1$ is complementary to a transcript capture probe which has been immobilized on a solid substrate. Subdomain $c_2$ is complementary to a labelling probe. After hybridization the amount of label retained is linearly proportional to the amount of analyte present in the original sample.

In an alternate embodiment the transcript of the C domain has only a $c_1$ subdomain. The C domain is transcribed in the presence of labelled ribonucleotide triphosphates and the labelled transcript is subsequently bound to an immobilized transcript capture probe through its complementary $c_1$ subdomain and quantified.

In yet another embodiment the transcript of the C domain has only a $c_2$ subdomain. The C domain is transcribed in the presence of biotinylated ribonucleoside triphosphates and the transcripts is captured on avidin beads. The transcript is then annealed to a labelling probe through its complementary $c_2$ subdomain and quantified.

Several other methods of labeling and detecting the transcript of the amplifying probe are possible, including the simultaneous use of labeled ribonucleotides and avidin/biotin coupling, and will be obvious to those skilled in the art.

The B and C domain of polymerase probes may be prepared by cloning, enzymatic assembly, chemical cross-linking techniques, direct chemical synthesis or a combination thereof. When prepared by cloning, nucleic acid sequences that encode the entire B/C domain or fragments thereof can be made in single- or double-stranded form by conventional cloning procedures.

The B domain is double stranded, and the C domain may be either single or double stranded. Double stranded domains can be created in two ways: The strands can be cloned separately and subsequently the complementary strands hybridized; or alternatively, the probe can be cloned as a single stranded, self-annealing polynucleotide (e.g.—b' c' c b). In this case four to ten additional nucleotides, preferably 5–7 nucleotides, are added to the sequence as a spacer between c and c' to allow for proper contouring of the double-stranded region when it is self-annealed. The spacer is usually poly-A, but may be modified to minimize hybridization cross-reactivity between various probes in the assay.

The A domain can be conjugated to the B/C domain through interposed linking agents such as nucleic acid, amino acid, carbohydrate or polyol bridges, or through other cross-linking agents. The B/C domain may be synthesized with a 5'-nucleic acid residue that have been derivatized to have a functional group that provides a linking site for the A domain, or the residue can be derivatized after the oligonucleotide has been synthesized to provide such a site. A preferred procedure for chemical cross-linking is to incorporate a $N^4$-modified cytosine base at the 5'-end of the polynucleotide as described in the commonly owned E.P.A. publication No. 0225807.

In a more preferred embodiment the conjugation of the B/C domain DNA to the A domain antibody can be conducted in a manner analogous to enzyme conjugation. The B/C domain is synthesized to contain an alkylamine moiety. The alkylamine is reacted with a heterobifunctional cross linking agent such as succinimidyl 4-(maleimidomethyl) cyclohexane-1-carboxylate (SMCC). After column purification, the DNA can be reacted specifically with sulfhydryl functionalities. An antibody may contain a reactive sulfhydryl (such as in reduced F(ab')$_2$ or may be modified to contain a sulfhydryl (such as when modified with N-succinimidyl 3-(2-pyridyldithio)propionate (SPDP) then reduced). Direct DNA-amine to antibody-amine conjugation is also possible with homobifunctional reagents, but is typically more difficult to control.

B—Multimer Probes

Another embodiment of the invention, is a DNA amplification probe (referred to as a "multimer probe") containing two functional domains, a first domain, A, which is the same as domain A of the polymerase probe described supra, and a second (M—FIG. 1-4) which comprises several repeating subunits. This probe, like the polymerase probe described supra, is also used for signal amplification in immunoassays.

The polynucleotide of the M domain may be a linear or branched polymer of the same repeating single-stranded oligonucleotide subunit or different single-stranded oligonucleotide subunits. These subunits are capable of hybridizing specifically and stably to a single-stranded nucleotide of interest, typically a labeled oligonucleotide or another multimer. These units will normally be 15 to 50, preferably 15 to 30, nucleotides in length and have a GC content in the range of 40% to 60%. The total number of oligonucleotide units in the multimer will usually be in the range of 3 to 50, more usually 10 to 20. The oligonucleotide units of the multimer may be composed of RNA, DNA, modified nucleotides or combinations thereof.

The oligonucleotide subunits of the multimer may be covalently linked directly to each other through phosphodiester bonds or through interposed linking agents such as nucleic acid, amino acid, carbohydrate or polyol bridges, or through other cross-linking agents that are capable of cross-linking nucleic acid or modified nucleic acid strands. The site(s) of linkage may be at the ends of the subunit (in either normal 3'–5' orientation or randomly oriented) and/or at one or more internal nucleotides in the strand.

In linear multimers the individual subunits are linked end-to-end to form a linear polymer. In one type of branched multimer three or more oligonucleotide units emanate from a point of origin to form a branched structure. The point of origin may be another oligonucleotide subunit or a multifunctional molecule to which at least three units can be covalently bound. In another type, there is an oligonucleotide subunit backbone with one or more pendant oligonucleotide subunits. These latter-type multimers are "fork-like", "comb-like" or combination "fork-" and "comb-like" in structure. The pendant units will normally depend from a modified nucleotide or other organic moiety having appropriate functional groups to which oligonucleotides may be conjugated or otherwise attached. See FIG. 1D.

The multimer may be totally linear, totally branched, or a combination of linear and branched portions. Preferably there will be at least two branch points in the multimer, more preferably at least 15, preferably 15 to 50. The multimer may include one or more segments of double-stranded sequences.

Domain M may be prepared by cloning (if linear), enzymatic assembly, chemical cross-linking techniques, direct chemical synthesis or a combination thereof. These methods of synthesis are fully disclosed in the commonly owned international application, Pub. No. 89/03891, published 5 May 1989. In the case of linear multimers prepared by cloning, nucleic acid sequences that encode the entire multimer or fragments thereof can be made in single- or double-stranded form by conventional cloning procedures. When made in double-stranded form, the multimers/fragments are ultimately denatured to provide single-stranded multimers/fragments. Multimers may be cloned in single-stranded form using conventional single-stranded phage vectors such as M13. Fragments can be linked enzymatically or chemically to form the domain M multimer. When assembled enzymatically, the individual units are ligated with a ligase such as T4 DNA or RNA ligase, as the case may be. When prepared by chemical cross-linking, the individual units may be synthesized with one or more nucleic acids that have been derivatized to have functional groups that provide linking sites or derivatized after the oligonucleotide has been synthesized to provide such sites. A preferred procedure for chemical cross-linking is to incorporate $N^4$-modified cytosine bases into the nucleotide as described in commonly owned E.P.A. No. 225 807, the disclosure of which is incorporated herein by reference.

When prepared by direct chemical synthesis oligonucleotides containing derivatized nucleic acids or equivalent multifunctional molecules whose functional groups are blocked are made by conventional oligonucleotide synthesis techniques. The functional groups are unblocked and oligonucleotide units are synthesized out from the unblocked site(s).

A generic structure for the molecules used to generate branch points in the multimers is as follows:

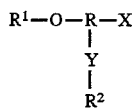

Figures 2, 4:
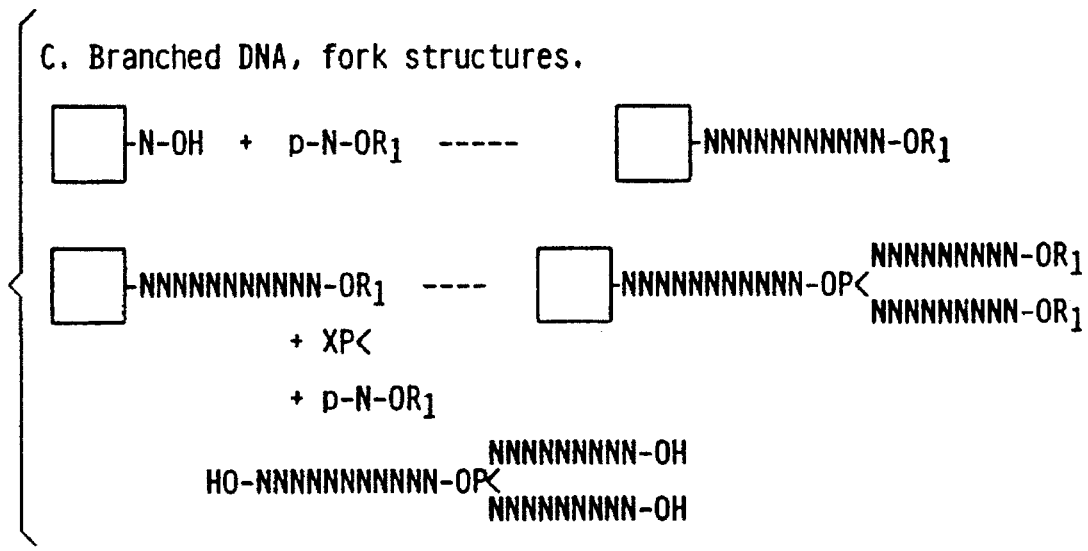
Figures 3, 4:
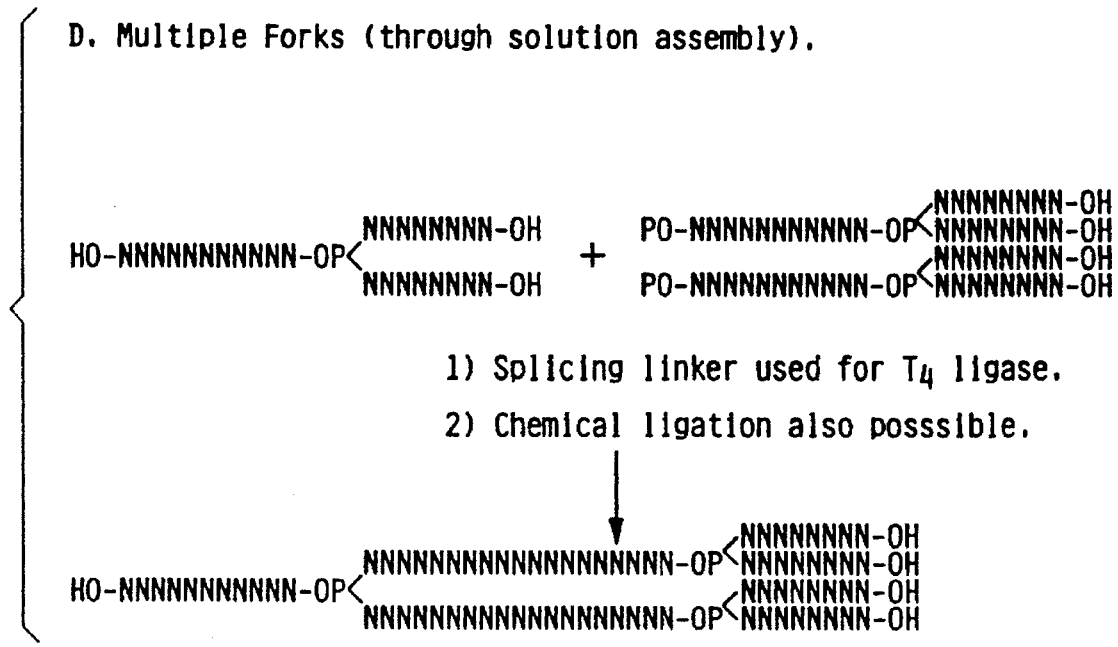
Figure 4:
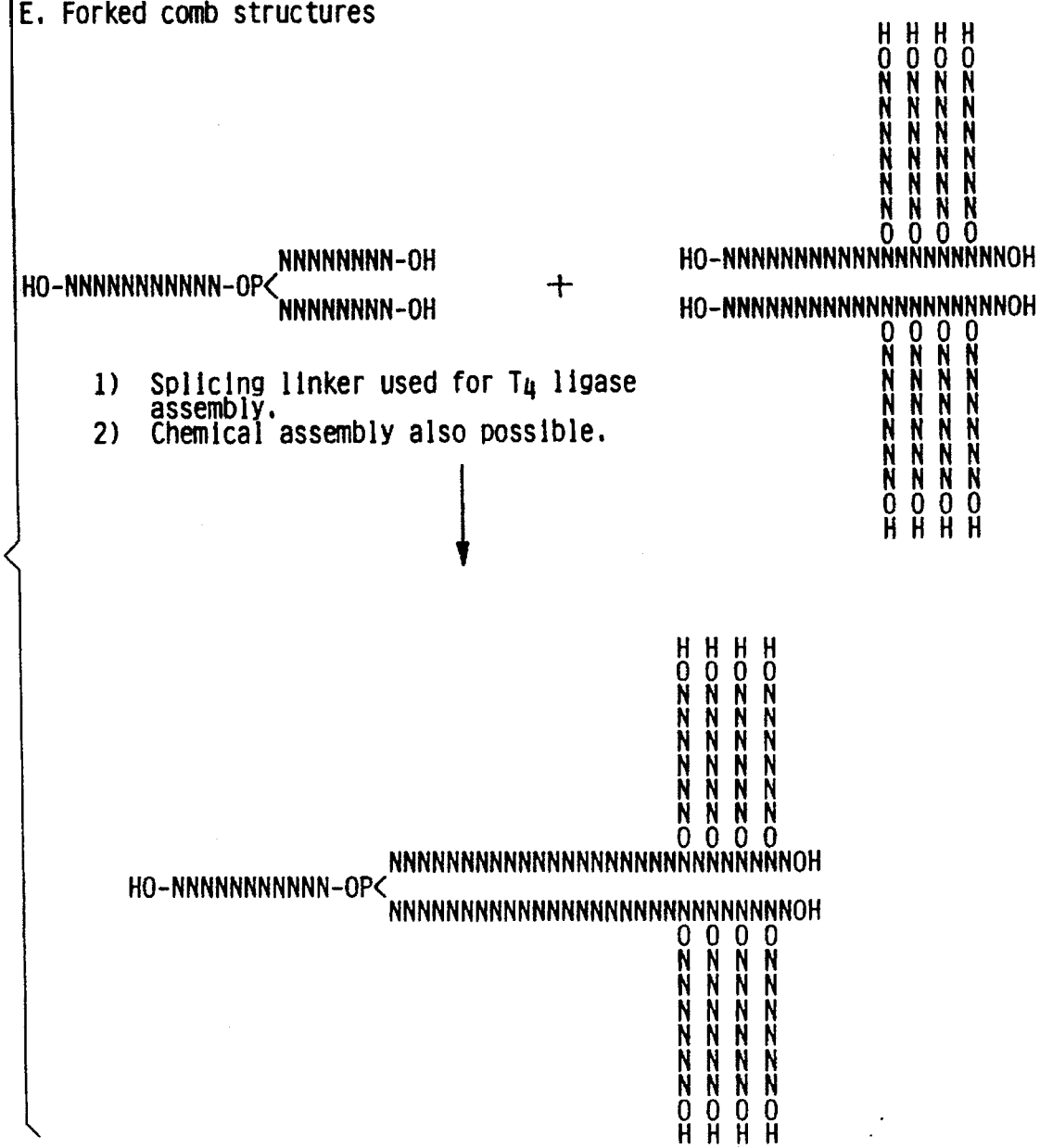
Figures 4, 5:
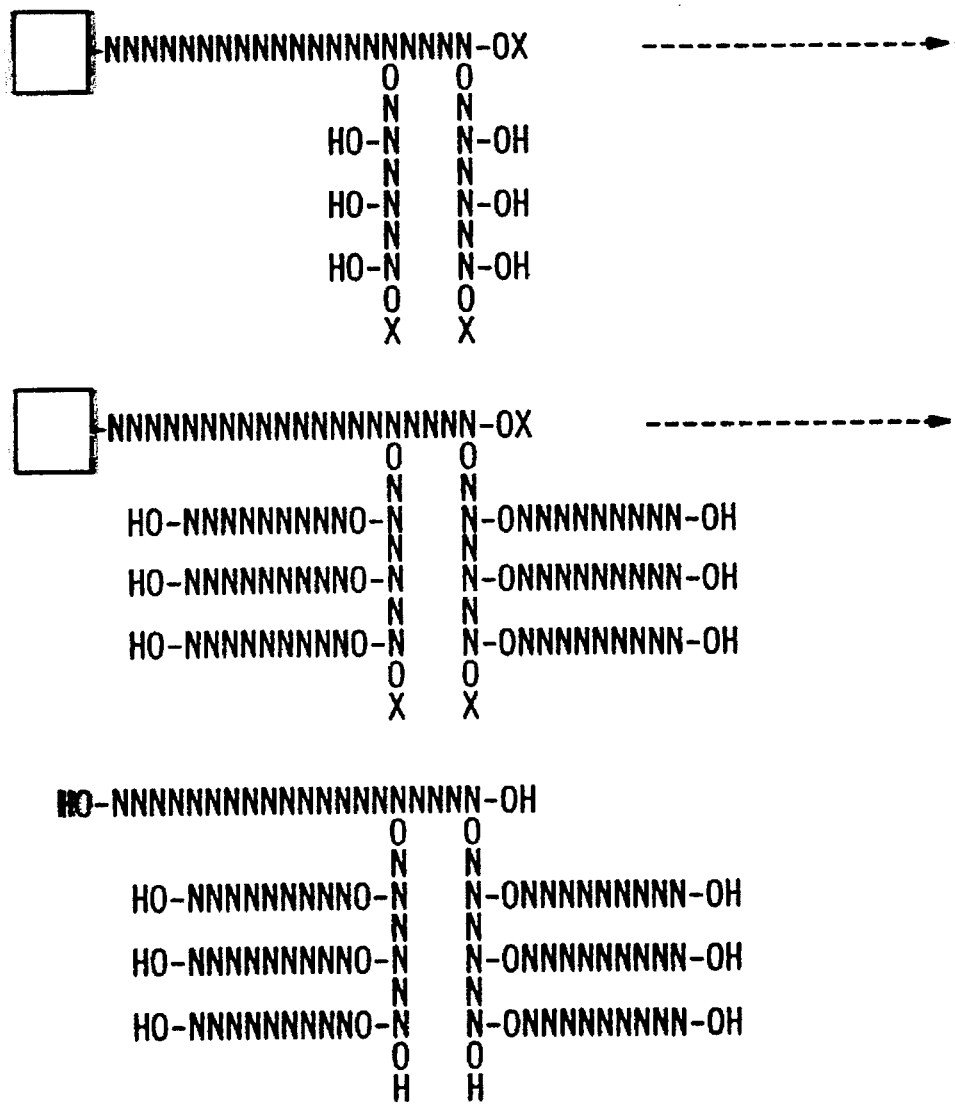

(1)

where R is an organic moiety, preferably a nucleic acid, $R^1$ is a hydroxyl protecting group that can be removed under conditions that do not remove synthetic nucleic acid from a solid phase and do not remove exocyclic nitrogen or phosphate protecting groups, X is a phosphorus-containing group that facilitates nucleic acid synthesis, such as a protected phosphoramidite, phosphonate or phosphate group, Y is a radical derived from a nucleophilic group such as an amino, hydroxyl, sulfhydryl or protected phosphate, and $R^2$ is $R^1$ or a blocking or protective group that can be removed and replaced with hydrogen without affecting $R^1$. In molecules used to generate bifurcated or "fork-like" branching, $R^1$ and $R^2$ are the same; whereas in molecules used to generate "comb-like" branching, $R^2$ is a blocking group that is stable in the presence of an $R^1$ deblocking reagent. FIG. 4 schematically illustrates the procedures used to synthesize multimers having "comb-like" branches, "fork-like" branches, or combinations thereof.

FIG. 4-1 depicts a conventional oligonucleotide synthesis scheme for preparing a linear oligonucleotide, such as the automated phosphoramidite method (Warner et al., DNA (1984) 3:401). The dark block represents a solid support, N represents a nucleotide and p-N-OR$_1$ (R$_1$ is equivalent to $R^1$ below), a conventional nucleotide derivative having appropriate protecting groups.

FIG. 4-2 shows the procedure for making a comb-like multimer. The compound:

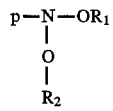

represents a modified base of formula (2) below. An oligomer unit of desired size and sequence is synthesized and left on the support. One or more $N^4$-modified cytosine bases are then incorporated into the chain by said automated procedure. Preferably, the modified base has the formula:

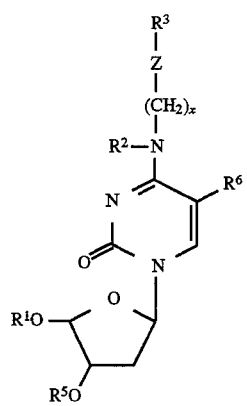

(2)

where Z is a nucleophile such as —O—, —NH—, —S—, $PO_4\!=\!$, and

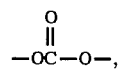

$R^1$ is a blocking or protective group such as dimethoxytrityl (DMT) or pixyl that is generally base-stable and acid sensitive, $R^2$ is hydrogen or methyl, $R^3$ is a blocking or protective group that can be removed and replaced with hydrogen without affecting $R^1$ such as

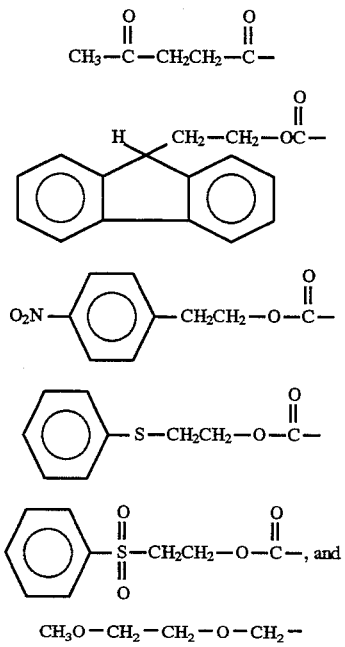

$R^5$ is a phosphoramidite or other phosphorus derivative that enables addition of nucleotides to the 5' position of an oligonucleotide chain during chemical synthesis (e.g., a phosphodiester, phosphotriester, etc.), $R^6$ is methyl, hydrogen, I, Br, or F, and X is an integer in the range of 1 to 8, inclusive. When more than one modified base is incorporated they are preferably spaced by intermediate bases in the chain, most preferably by a -TT- dimer. Additional oligonucleotide units may be incorporated into the backbone followed by additional modified bases and so forth.

The $N^4$ nucleophile group is then deprotected ($R^3$ is removed) and additional oligonucleotide units are generated therefrom by the automated procedure. Residual $R^1$ groups at the chain termini are removed and the branched "comb-like" multimer is cleaved from the support.

FIG. 4-3 depicts the general procedure for making "fork-like" multimers. Again, an oligomer unit of desired size and sequence is synthesized by conventional techniques and left on the support. A blocked, bifunctional phosphorus-containing group (represented as XP in FIG. 4-3) such as a blocked phosphoramidite, is then incorporated into the chain by the automated procedure. Preferred bifunctional phosphorus-containing groups are blocked phosphoramidites of the formula

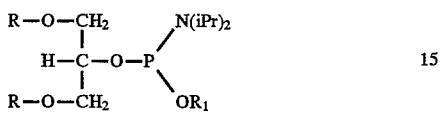

where R is said hydroxyl protecting group, iPr is isopropyl, and $R^1$ is methyl or beta-cyanoethyl. Most preferably R is DMT and $R^1$ is beta-cyanoethyl.

Alternatively, the $N^4$-modified cytosine base where $R_1=R_2$ (e.g., DMT) can be used.

The two protecting groups are then removed and additional oligonucleotide units are generated therefrom by the automated procedure. Residual $R^1$ groups are removed and the bifurcated multimer is cleaved from the support.

Parts D and E depict procedures where two or more bifurcated multimers, "comb-like" multimers or combinations thereof are spliced together enzymatically or chemically. Generally, the bifurcated and/or "comb-like" multimers are prepared as above and removed from the support. They are then combined in solution using the enzymatic or chemical linkage procedures described above.

Part F shows the procedure for synthesizing a multiple "comb-like" multimer. This procedure is a variation of the procedure shown in Part B and involves incorporating modified bases in the dependent side chains and generating secondary oligonucleotide side chains therefrom.

Suitable cleavable linker molecules may be incorporated into the multimers at predetermined sites for the purpose of analyzing the structure of the multimer or as a means for releasing predetermined segments (such as the portion of the multimer that binds to the labeled oligonucleotide). Subsequent to multimer synthesis and purification these linkers can be cleaved specifically without additional degradation of the nucleotide structure of the multimer. A preferred type of linker molecule was designed to contain a 1,2-diol group (which can be cleaved selectively by periodates) as well as a protected hydroxyl and phosphoramidite derived hydroxyl group to permit the linker to be incorporated into any DNA fragment by standard phosphoramidite chemistry protocols. A preferred embodiment of such a linker is the compound:

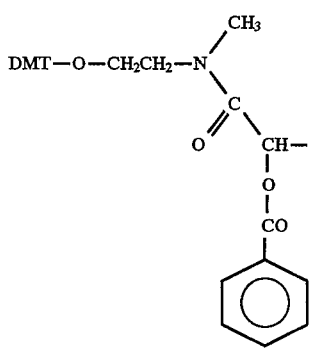

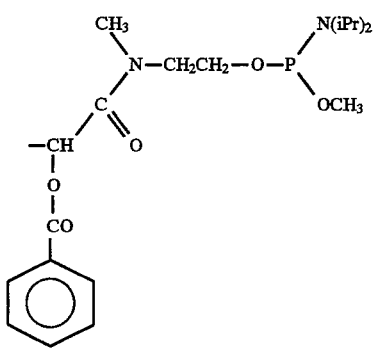

where DMT and iPr are as defined previously. After incorporation into a DNA fragment and complete deprotection the linker-containing fragment has the following structure:

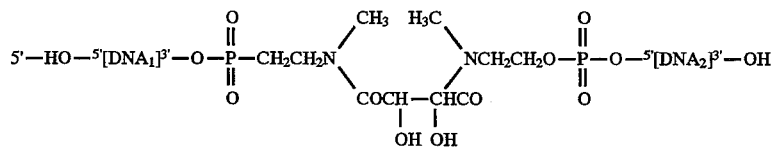

where $DNA_1$ and $DNA_2$ represent DNA subfragments which may be the same or different. Reaction of this fragment with sodium periodate cleaves the fragment into the following subfragments:

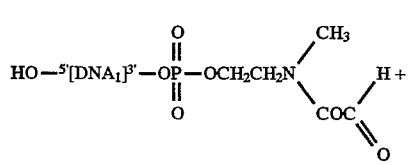

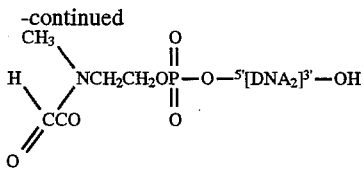

Alternatively, the 1,2-diol group may be replaced with linker groups that contain a hydroxylamine-sensitive linkage, a base-sensitive sulfone linkage, or a thiol-sensitive disulfide linkage. Such linker groups may be derived from conventional cross-linking agents that are used to conjugate proteins to other entities. Likewise, protecting groups other than DMT may be used.

The functional aspects of the polymerase probe may be combined with the multimer probe structure by synthesizing a multimer probe having a M domain with subunits comprising multiples of the promoter/template (B/C) domains of the polymerase probe. Like multimer probes the multimeric subunits may be either in a linear array or branched molecules.

Like polymerase probes, the A domain of multimer probes can be conjugated to the M domain through interposed linking agents such as nucleic acid, amino acid, carbohydrate or polyol bridges, or through other cross-linking agents. The M domain may be synthesized with a 5'-nucleic acid residue that has been derivatized to have a functional group that provides a linking site for the A domain, or the residue can be derivatized after the oligonucleotide has been synthesized to provide such a site. A preferred procedure for chemical cross-linking is to incorporate a N4-modified cytosine base at the 5'-end of the polynucleotide as described in the commonly owned E.P.A. publication No. 0225807 and in Section I(A), supra.

II—Immunoassays

Another aspect of this invention employs amplifier probes in immunoassays to detect and quantify the presence and concentration of an immunologic analyte. These amplifier probes are of two classes: the hybrid probes disclosed in Sec. I Supra (either polymerase probes or multimer probes); or the polynucleotide probes disclosed in U.S. Ser. No. 463,022 and U.S. Ser. No. 340,031. These probes are similar to the hybrid probes, but with A domains comprised of a polynucleotide sequence rather than a polypeptide.

The analyte may be any known immunogen of interest. The analyte may be present in low concentration in a prepared sample or it may be a minority species in a heterogeneous mixture of biological material. The analyte may be present in a variety of sources, e.g., biological fluids or tissues, food stuffs, environmental materials, etc., or it may be synthesized in vitro.

In a first step, the sample containing the analyte is prepared by any of a variety of methods known to those skilled in the art.

Amplifier probes can be employed to detect an analyte in any number of immunoassay protocols—conducted either in solution or immobilized upon a solid phase. If the immunoassay is conducted in solution, the sample containing the analyte is either bound to the amplifier probe directly; indirectly through one or more antibodies specific for the analyte; or, if a polynucleotide probe is employed, in conjunction with a hybrid linker molecule (discussed in Sec II(B), infra). Amplifier probes can be utilized in this fashion in most soluble immunoassay protocols. See, for example, U.S. Pat. No. 4,778,751.

In an immunoassay utilizing a solid phase, the analyte (which either be an antigen or an antibody) is either immobilized directly upon a solid phase; indirectly by binding the analyte to a first antibody that has first been bound to a solid phase; or by a sandwich assay (FIG. 2-1) in which a second antibody recognizes the analyte and in turn is recognized by the first antibody bound to the solid phase.

If the analyte is to be directly bound to a solid phase, the sample containing analyte is contacted with a nitrocellulose filter or similar means for non-selectively binding protein. If the analyte is to be indirectly and selectively bound to a solid phase a first antibody, directed to an epitope of the analyte or to a second antibody, is conjugated to the solid phase and subsequently used to bind the analyte or a second antibody bound to the analyte.

A—Using Hybrid Probes

An additional antibody, directed to a second epitope of the analyte can then be employed as a linker between the analyte and an amplifier probe. The amplifier probe, either a polymerase probe or a multimer probe, whose A domain is directed to the second antibody, can then be conjugated to the linker antibody, forming a string consisting of the first antibody bound to a solid phase, a second antibody, the analyte, a linker antibody, and the amplifier probe (FIG. 2-7).

B—Using Polynucleotide Probes

In an alternate embodiment, the amplifier probe employed is one of the polynucleotide multimer probes disclosed in International Publication No. 89/03891. These probes differ from the peptide/nucleotide-hybrid multimer probes of the instant application in that domain A is a polynucleotide sequence rather than a antibody-functioning polypeptide. Consequently, an antibody/polynucleotide hybrid linker must be employed to indirectly couple the analyte to the amplifier probe (FIG. 2-2). This hybrid linker has a first domain, which is a polypeptide that functions as an antibody specific for an epitope of the analyte or an epitope of an antibody which recognizes the analyte; and a second domain which is a nucleotide sequence substantially complementary to the nucleotide sequence of the A domain of the amplifier probe.

Similarly, in an alternate embodiment, one of the polynucleotide polymerase probes disclosed in U.S. application Ser. No. 463,022 may be employed. These probes differ from the hybrid polymerase probes of the instant application in that domain A is a polynucleotide sequence rather than a antibody functioning polypeptide. These probes also require the use of a hybrid linker as described supra.

By using a polynucleotide amplifier probe and a hybrid linker rather than the hybrid amplifier probes described in Section I, supra, the amplifier probe can be a "universal" reagent, useful for both nucleic acid hybridization assays and immunoassays.

C—Binding and Hybridization Conditions

In a preferred embodiment, the analyte is indirectly immobilized upon a solid phase, for example a 96-well polyvinyl chloride (PVC) plate. In the sandwich assay depicted in FIG. 2-1, 50 μl of the first antibody (anti-rabbit at a concentration of 20 μg/ml in 0.2M $NaHCO_3$) is added to a well. The well is covered and incubated for 2 hours at room temperature in a humidified atmosphere. The solution is then aspirated from the well. The well is then washed twice with a blocking buffer comprising 3% bovine serum albumin in phosphate buffered saline solution containing 0.02% sodium azide. The well is next incubated with blocking buffer for 20 minutes at room temperature in a humidified atmosphere and then washed twice more with blocking buffer.

50 μl of the second antibody (rabbit-anti analyte also at a concentration of 20 μg/ml) is added to the well and the procedure described above is repeated. Next series of dilutions, in blocking buffer, of the analyte is prepared. 50 µl of each dilution is added to a well. The plate is covered and incubated for 2 hours at room temperature in a humidified atmosphere. Following this incubation the wells are washed four times with blocking buffer. The third antibody (mouse-anti-analyte) is next added in the same fashion, followed by addition of the hybrid amplifier probe. Since occasional tissue preparations may contain anti-DNA antibodies, the blocking buffer used for the washes which follow the addition of the probe also contains 20 µg/ml salmon sperm DNA.

When polynucleotide amplifier probes or hybrid multimer probes are used, a nucleic acid hybridization step follows the complexing of the analyte and antibodies. Usually, hybridization conditions consist of an aqueous medium, particularly a buffered aqueous medium, which includes various additives. These additives can include the polynucleotides to be hybridized, salts (e.g. sodium citrate 0.017M to 0.17M and/or sodium chloride 0.17M to 1.7M), non-ionic detergents such as NP-40 or Triton X-100 (0.1 to 1.0%) which do not interfere with the antigen/antibody complex, and carrier nucleic acids. The mixture is incubated for 15 to 75 minutes at 35° C. to 55° C.

If the conditions employed for hybridization of the labeled oligonucleotide to the multimer subunits causes instability in the antigen/antibody complexes, the hybridization step can be preceded by treatment of the complex with a protein crosslinker such as glutaraldehyde, or a similar method of stabilizing the complex. Once the protein complex is stabilized, conditions of nucleic acid hybridization may be altered to include SDS (up to 1%); nonaqueous solvents such as dimethylformamide, dimethylsulfoxide, and formamide; and temperatures up to 70° C.

It is important to adjust nucleic acid hybridization conditions to maintain the stability of the antigen/antibody complexes. For example, the hybridization of shorter stretches of complementary sequences can be accomplished at lower temperatures. In a preferred embodiment, complementary single-stranded regions are 12 to 20 bases. In a preferred embodiment, the hybridization temperature is 35 to 45 degrees C. Furthermore, since the only single-stranded oligonucleotides present at this step are the complementary strands, higher stringency and consequently lower salt concentrations (0.3M Na) can be tolerated.

1—Multimer Probe

If a multimer probe is employed, labeled oligonucleotide which is substantially complementary to the repeating polynucleotide of the M domain is subsequently added under conditions which permit it to hybridize to the complementary oligonucleotide units of the multimer. The resulting solid phase labeled nucleic acid complex is then separated from excess labeled oligonucleotide, by washing to remove unbound labeled oligonucleotide, and read.

The amplification may be multiplied by the use of more than one species of multimer (as defined by subunit sequence) in the assay. In such instances a second multimer is designed to bind to the repeat sequence of the first multimer and the complex is subsequently labeled with an oligonucleotide that is substantially complementary to the repeat sequence of the second multimer. Any number of multimers may be bound in series in this manner to achieve even greater amplification.

2—Polymerase Probe

If a polymerase probe is employed, the RNA polymerase specific for the promoter region (domain B) of the amplifier probe is next added under appropriate transcription conditions and multiple RNA copies (c) of the C domain template (c') are produced. The amount of transcript is proportional to the quantity of the analyte in the initial preparation.

Transcription conditions consist of an aqueous medium, preferably a buffered aqueous medium, with appropriate salts, usually including a magnesium salt, rATP, rUTP, rGTP, rCTP, a RNA polymerase enzyme and usually include various denaturing agents, protein carriers, and RNAse inhibitors. Incubation is usually for 15 to 90 minutes, usually 60 minutes; and at a temperature which is optimal for the chosen enzyme, usually 35° C. to 42° C., usually 37° C.

The sequence of the C domain is designed for a specific detection scheme and several such schemes may be employed to quantify the transcripts. For example, the transcription product (c) of the C domain may be subdivided into 2 subdomains—$c_1$ and $c_2$ (FIG. 2-2). Subdomain $c_1$ is complementary to a transcript capture probe which has been immobilized on a solid substrate. Subdomain $c_2$ is complementary to a labelling probe. After hybridization the amount of label retained is linearly proportional to the amount of analyte present in the original sample.

In an alternate embodiment the transcript of the C domain has only a $c_1$ subdomain. The C domain is transcribed in the presence of labelled ribonucleotide triphosphates and the labelled transcript is subsequently bound to an immobilized transcript capture probe through its complementary $c_1$ subdomain and quantified.

In yet another embodiment the transcript of the C domain has only a $c_2$ subdomain. The C domain is transcribed in the presence of biotinylated ribonucleoside triphosphates and the transcripts is captured on avidin beads. The transcript is then annealed to a labelling probe through its complementary $c_2$ subdomain and quantified.

Several other methods of labeling and detecting the transcript of the amplifying probe are possible, including the simultaneous use of labeled ribonucleotides and avidin/biotin coupling, and will be obvious to those skilled in the art.

3—General Considerations

The solid phase that is used in the assay may be particulate or be the solid wall surface of any of a variety of containers, e.g., centrifugal tubes, columns, microtiter plate wells, filters, tubing, etc. Preferably, particles will be employed of a size in the range of about 0.4 to 200 microns, more usually from about 0.8 to 4.0 microns. The particles may be any convenient material, such as latex, or glass. The first antibody specific for the analyte, or for a second antibody which is specific for the analyte, may be stably attached to the solid surface through functional groups by known procedures.

The labeling probes will, if polymerase probes are employed, include sequences complementary to the $c_2$ subdomain of the transcripts of the amplifier probe; and if multimer probes are employed, labeling probes will include sequences complementary to the repeating units of the B domain. The labelling probe will include one or more molecules ("labels"), which directly or indirectly provide for a detectable signal. The labels may be bound to individual members of the complementary sequence or may be present as a terminal member or terminal tail having a plurality of labels. Various means for providing labels bound to the sequence have been reported in the literature. See, for example, Urdea et al, *Nucl. Acids Res.* (1988) 16:4937, Leary et al., *Proc. Natl. Acad. Sci. USA* (1983) 80:4045; Renz and Kurz, *Nucl. Acids Res.* (1984) 12:3435; Richardson and Gumport, *Nucl. Acids Res.* (1983) 11:6167; Smith et al., *Nucl. Acids Res.* (1985) 13:2399; Meinkoth and Wahl,

*Anal. Biochem.* (1984) 138:267. The labels may be bound either covalently or non-covalently to the complementary sequence. Labels which may be employed include radionuclides, fluorescers, chemiluminescers, dyes, enzymes, enzyme substrates, enzyme cofactors, enzyme inhibitors, enzyme subunits, metal ions, and the like. Illustrative specific labels include fluorescein, rhodamine, Texas red, phycoerythrin, umbelliferone, luminol, NADPH, galactosidase, horseradish peroxidase, etc. See Urdea et al for a comparison of non-radioisotopic labelling methods.

The labelling probes can be conveniently prepared by chemical synthesis such as that described in commonly owned E.P.O. Pub. No. 225807. By providing for a terminal group which has a convenient functionality, various labels may be joined through the functionality. Thus, one can provide for a carboxy, thiol, amine, hydrazine or other functionality to which the various labels may be joined without detrimentally affecting duplex formation with the sequence. As already indicated, one can have a molecule with a plurality of labels joined to the sequence complementary to the labeling sequence. Alternatively, one may have a ligand bound to the labeling sequence and use a labeled receptor for binding to the ligand to provide the labeled analyte complex.

Depending upon the nature of the label, various techniques can be employed for detecting the presence of the label. For fluorescers, a large number of different fluorometers are available. With enzymes, either a fluorescent or a colored product can be provided and determined fluorometrically, spectrophotometrically or visually. The various labels which have been employed in immunoassays and the techniques applicable to immunoassays can be employed with the subject assays.

The procedure used in the separation steps of the assay will vary depending upon the nature of the solid phase. For particles, centrifugation or filtration will provide for separation of the particles, discarding the supernatant or isolating the supernatant. Where the particles are assayed, the particles will be washed thoroughly, usually from one to five times, with an appropriate buffered medium containing detergent, e.g., PBS with SDS. When the separation means is a wall or support, the supernatant may be isolated or discarded and the wall washed in the same manner as indicated for the particles.

D. Competitive Immunoassays

The hybrid amplifier probes of the subject invention can also be employed as a means for labeling antigen in a competitive immunoassay. In the typical assay, excess antibody, polyclonal or monoclonal, preferably monoclonal, which specifically binds to the analyte, is immobilized upon a solid phase, usually in a multiple well plate. A standard concentration of labeled antigen is mixed with serial dilutions of a sample thought to contain an unknown amount of analyte. The separate dilutions are then exposed to the immobilized antibody and the amount of bound label is measured. The ability of the unlabeled analyte to compete with the labeled analyte is used to calculate the amount of analyte in the sample.

In one embodiment, a B/C domain polynucleotide moiety of the polymerase probe is conjugated to a competitive immunogen. This hybrid molecule is then used as the labeled antigen described supra. After the competitive binding, polymerase (specific for the B domain promoter) is added and the transcription product is assayed as described in Section I(A), supra.

In another embodiment, a M domain polynucleotide moiety of the multimer probe is conjugated to a competitive immunogen. This hybrid molecule is then used as the labeled antigen described supra. After the competitive binding, the M domain is labeled and quantified as described, supra.

For immunogen coupling to DNA, homobifunctional reagents such as disuccinimidyl suberate (DSS), ethylene glycol bis(succinimidylsuccinate) (EGS), or p-phenylene diisothiocyanate (DITC), are probably more useful coupling methods than those described in Section I(A), supra.

Kits for carrying out amplified immunoassays according to the invention will comprise, in packaged combination, the following reagents: a solid phase that is either capable of binding the antigen analyte or alternatively already has a linking first antibody bound to it if the assay format is one in which the analyte is indirectly bound to the solid phase through a bound first antibody or through a second antibody; optionally linker second and third antibodies which are specific for the analyte, and a hybrid linker probe if the assay format is one in which a polynucleotide amplifier probe is used; the amplifier probe; the appropriate DNA-directed RNA polymerase and immobilized transcription capture probes (if a polymerase amplifier probe is used); and an appropriate labelling probe; These reagents will typically be in separate containers in the kit. The kit may also include hybridization buffers, wash solutions, negative and positive controls and written instructions for carrying out the assay.

The following examples are presented as illustrations, not limitations, of the present invention. Other embodiments within the spirit and scope of the invention will suggest themselves to those skilled in the art.

EXAMPLE 1

Immunoassay for the Presence of an HCV Antigen in Human Serum

This assay is designed to test directly for the presence of the C-100 antigen of the Hepatitis C virus. The general protocol for this immunoassay is as described, supra. Microtiter plates are prepared using goat-anti-mouse as the first antibody. This antibody is immobilized in the wells of a 96-well microtiter plate. The second antibody is a mouse monoclonal antibody specific for an epitope of HCV C-100. Duplicate dilutions of serum from individuals to be screened for HCV are prepared in blocking buffer and incubated in the microtiter wells along with appropriate non-infected controls. The third antibody is a combination of polyclonal rabbit-antibodies which recognizes each of the HCV antigens. The final antibody is a hybrid T7 polymerase amplifier probe. The domain A polypeptide moiety functions as a goat-anti-rabbit antibody and completes the immunoassay "sandwich".

After addition of the T7 polymerase probe, transcription of domain C is effected by incubating the complex in 20 µl of a solution containing 40 mM Tris HCl (pH 8), 20 mM $MgCl_2$, 10 mM NaCl, 1 mM Spermidine, 10 mM Dithiothreitol, 0.15 mg/ml Bovine Serum Albumin, 1.25 mM each of rATP, rCTP, rGTP, rUTP, 1600 units/ml RNasin, and 2000 units/ml T7 RNA polymerase. This mixture is incubated at 37° C. for 1 hour. Transcription is terminated by addition of 20 µl of a solution containing 8× SSC, and 0.2% SDS and the entire mixture is transferred to new wells containing an immobilized capture probe with $c_1'$ sequences. Capture of the domain C transcripts (FIG. 3) is effected by incubation at 55° C. for 1 hour followed by two washes with 0.1× SSC, 0.1% SDS.

The domain C transcripts are then labelled by addition of 50 fmol of enzyme-labeled probe ($c_2'$) in 40 µl of 4× SSC, 100 μg/ml poly A for 15 min. at 55° C. Finally, the complex was washed twice with 0.1× SSC, 0.1% SDS, followed by two washes with 0.1× SSC.

For AP detection, an enzyme-triggered dioxetane reaction (Schapp et al. (1987) Tet. Lett. 28: 1159–1162 and U.S. Pat. No. 4,857,652), obtained from Lumigen Inc., is employed. The detection procedure is as follows. For the labeling step 20 μl HM buffer with the AP probe is added to each well and the wells are incubated at 55° C. for 15 min. The supernatant is removed and the wells are washed 2× with 380 μl of 0.1× SSC and 0.1% SDS. The wells are then washed 2× with 380 μl of 0.1× SSC to remove any remaining SDS. 20 μl of $3.3 \times 10^{-4}$M dioxetane in CTAB buffer is added to each well. The wells are tapped lightly so that the reagent falls to the bottom and gently swirled to distribute the reagent evenly over the bottom. The wells are covered with the microtiter plate sealer and incubated in a 37° C. oven for one hour. The wells are then read with a luminometer, and quantified relative to a standard curve generated with known amounts of antigen.

EXAMPLE 2

Immunoassay for the Presence of Antibody to HCV in Human Serum

Microtiter plates are first coated with the HCV C-100 antigen from the Hepatitis C virus. A solution containing coating buffer (50 mM Na Borate, pH 9.0), 21 ml/plate, BSA (25 μg/ml), HCV C-100 (2.50 μg/ml) is prepared just prior to addition. After mixing for 5 minutes, 0.2 ml/well of the solution is added to the plates, they are covered and incubated for 2 hours at 37° C., after which the solution is removed by aspiration. The wells are washed once with 0.4 ml wash buffer (100 mM Na phosphate,pH 7.4, 140 mM NaCl, 0.1% casein, 1% (w/v) Triton X-100, 0.01% (w/v) Hibitane). After removal of the wash solution, 200 μl/well of Postcoat solution (10 mM Na phosphate, pH 7.2, 150 mM NaCl, 0.1% (w/v) casein, 3% sucrose and 2 mM phenylmethylsulfonylfluoride (PMSF), is added, the plates are loosely covered to prevent evaporation, and are allowed to stand at room temperature for 30 minutes. The wells are then aspirated to remove solution, and lyophilized dry overnight, without shelf heating.

To perform the immunoassay, 20 μl of duplicate dilutions of serum samples or controls are added to wells containing 200 μl of sample diluent (100 mM Na phosphate, pH 7.4, 500 mM NaCl, 1 mM EDTA, 0.1% (w/v) casein, 0.01% (w/v) Hibitane, 1% (w/v) Triton X-100, 100 μg/ml yeast extract). The plates are sealed, and incubated at 37° C. for 2 hours, after which the solution is removed by aspiration, and the wells are washed 3 times with 400 μl of wash buffer (PBS containing 0.05% Tween 20).

Subsequent to the addition of serum samples, the wells are treated as in Example 1, above, except that rabbit-antihuman serum is substituted for the third antibody (rabbit-anti-analyte).

EXAMPLE 3

Use of Multimer Probes in the Detection of HCV Infection

In either of the two examples above, multimer probes can be substituted for polymerase probes. All steps are the same in each example up through the addition of amplifier probe, except of course that a multimer probe is used rather than a polymerase probe. Subsequent to the binding of the amplifier probe, a solution of with 50 fmol of a labeled oligonucleotide sequence with substantial homology to the multimeric subunit of the M domain is added. This enzyme-labeled probe is added in 40 μl of 4× SSC, 100 μg/ml poly A for 15 min. at 55° C. Finally, the complex was washed twice with 0.1× SSC, 0.1% SDS, followed by two washes with 0.1× SSC.

For AP detection, an enzyme-triggered dioxetane reaction (Schapp et al. (1987) Tet. Lett. 28: 1159–1162 and U.S. Pat. No. 4,857,652), obtained from Lumigen Inc., is employed. The detection procedure is as follows. For the labeling step 20 μl HM buffer with the AP probe is added to each well and the wells are incubated at 55° C. for 15 min. The supernatant is removed and the wells are washed 2× with 380 μl of 0.1× SSC and 0.1% SDS. The wells are then washed 2× with 380 μl of 0.1× SSC to remove any remaining SDS. 20 μl of $3.3 \times 10^{-4}$M dioxetane in CTAB buffer is added to each well. The wells are tapped lightly so that the reagent falls to the bottom and gently swirled to distribute the reagent evenly over the bottom. The wells are covered with the microtiter plate sealer and incubated in a 37° C. oven for one hour. The wells are then read with a luminometer, and quantified relative to a standard curve generated with known amounts of antigen.

EXAMPLE 4

Use of Polynucleotide Polymerase Probes in the Detection of HCV Infection

In either of Examples 1 or 2 above, polynucleotide polymerase probes can be substituted for the hybrid polymerase probes. All steps are the same in each example up through the addition of the third antibody which is a combination of polyclonal rabbit-antibodies which recognizes each of the HCV antigens. This is followed by addition of 50 μl of a hybrid linker molecule at a concentration of 20 μg/ml in 0.2M NaHCO$_3$. This incubation is conducted according to the same protocol as all previous antibody incubations. The hybrid linker molecule has a first domain which functions as an anti-rabbit antibody and binds to the all previously bound rabbit third-antibodies. The second domain of the hybrid linker is an oligonucleotide with 15 residues the sequence of which is substantially complementary to domain A of the polynucleotide polymerase probe. After incubation and washing the polymerase probe is added in 50 μl of hybridization buffer (0.3M NaCl, 0.1% NP-40) and incubate for 60 minutes at 40° C. After incubation excess probe is removed and the complex is washed 3 times with hybridization buffer. Domain B is transcribed and the transcription quantified as described in Example 1.

EXAMPLE 5

Use of Polynucleotide Multimer Probes in the Detection of HCV Infection.

This assay is identical to that described in Example 4, up through the addition of the polynucleotide probe. Subsequent hybridization of label to the domain M subunits and quantification of label is the same as in Example 3.

Other variations and applications of the various amplifier probes described in this application to methods of immunoassay will be obvious to those skilled in the art and are intended to be within the scope of the subject invention.

We claim:

1. A molecular probe for use as a signal amplifier in immunoassays comprising:
   (a) a first domain (A) which is a polypeptide and functions as an antibody specific for a known antigen;
   (b) a second domain (B) which is a double-stranded polynucleotide capable of functioning as a promoter for a DNA-dependent RNA polymerase enzyme activity; and (c) a third domain (C) which is either a single- or double-stranded polynucleotide with a random sequence, whose transcript is incapable of being translated into a polypeptide, and is directly 3' to the second domain, such that the third domain is a template for the promoter activity of the second domain, wherein said first domain is covalently conjugated to said second domain and said second domain is covalently conjugated to said third domain.

2. The probe of claim 1 in which the DNA-dependent RNA polymerase activity is derived from the bacteriophage T7.

3. The probe of claim 1 in which the DNA-dependent RNA polymerase activity is derived from the bacteriophage T3.

4. The probe of claim 1 in which the DNA-dependent RNA polymerase activity is derived from the bacteriophage SP6.

5. The probe of claim 1 in which the second domain B is at least 10 and no more than 40 nucleotides long.

6. The probe of claim 1 in which the second domain B is at least 20 and no more than 35 nucleotides long.

7. The probe of claim 5 in which the third domain C is at least 30 and no more than 80 nucleotides long.

8. The probe of claim 5 in which the third domain C is at least 35 and no more than 50 nucleotides long.

9. The probe of claim 2 in which the sequence for the second domain B comprises the sequence:

5'-TAA TAC GAC TCA CTA TA-3'

3'-ATT ATG CTG AGT GAT AT-5'

10. The probe of claim 2 in which the nucleotide sequence of the second domain B is:

5'-CTG GCT TAT CGA AAT TAA TAC GAC TCA CTA TA-3'

3'-GAC CGA ATA GCT TTA ATT ATG CTG AGT GAT AT-5'

11. The probe of claim 1 in which the 3' end of the template is adjacent to the second domain B, and is a cytosine residue.

12. The probe of claim 1 in which the sequence for the third domain C is:

5'-GGG AGA TGT GGT TGT CGT ACT TAG CGA AAT ACT GTC CGA GTC G-3'

3'-CCC TCT ACA CCA ACA GCA TGA ATC GCT TTA TGA CAG GCT CAG C-5'

13. The probe of claim 1 in which the transcript of the third domain C has two subdomains:

(a) a first subdomain, $c_1$, which is capable of hybridizing to an oligonucleotide capture linker, the capture linker being capable of hybridizing to a polynucleotide immobilized on a solid substrate; and (b) a second subdomain, $c_2$, which is capable of binding to an oligonucleotide label linker, the label linker capable of binding to a quantifiable probe.

14. The probe of claim 1 in which a functional unit comprising the second and third domains, B and C, are present in multiple repeating units.

15. A molecular probe for use as a signal amplifier in immunoassays comprising:

(a) a first domain (A) comprising a polypeptide capable of functioning as an antibody which binds specifically to a known analyte; and (b) a second domain (M) comprising a multiplicity of single-stranded oligonucleotide subunits that are capable of hybridizing specifically to a single-stranded nucleic acid of interest, wherein said second domain (M) consists of a branched polynucleotide having a minimum of three termini, which are of the 3' or 5' type, and at least one covalent branch point, wherein the multiplicity of single-stranded oligonucleotide subunits are bonded directly or indirectly only via covalent bonds and wherein said first domain is covalently conjugated to said second domain.

16. The probe of claim 15 in which each oligonucleotide unit of the second domain M, comprises about 15 to 50 bases and has a GC content in the range of about 40% to about 60%.

17. The probe of claim 15 in which the probe is a comb-like multimer comprising an oligonucleotide backbone with one or more pendant chains composes of one or more oligonucleotide units.

18. The probe of claim 15 in which the first domain is conjugated to the second domain via a cross-linking agent.

19. The probe of claim 18 in which the cross-linking agent is covalently bonded to the oligonucleotide via the $N^4$-position of $N^4$-modified cytosine bases.

20. The probe of claim 15 wherein the second domain, M, contains one or more modified nucleotides.

21. The probe of claim 15 wherein the oligonucleotide subunits of the second domain are linked directly to each other through phosphodiester bonds.

22. The probe of claim 15 wherein the oligonucleotide subunits of the second domain are linked to each other via a cross-linking agent.

23. The probe of claim 22 wherein the cross-linking agent is covalently bonded to the oligonucleotide subunits of the second domain via the $N^4$-position of $N^4$-modified cytosine bases.

24. The probe of claim 15 wherein at least a portion of the oligonucleotide subunits of the second domain are linked via a multifunctional moiety derived from a compound of the formula:

where R is an organic moiety, preferably a nucleic acid, $R^1$ is a hydroxyl protecting group that can be removed under conditions that do not remove synthetic nucleic acid from a solid phase and do not remove exocyclic nitrogen or phosphate protecting groups, X is a phosphorus-containing group that facilitates nucleic acid synthesis, Y is a radical derived from a nucleophilic group, and $R^2$ is $R^1$ or a blocking or protective group that can be removed and replaced with hydrogen without affecting $R^1$.

25. The probe of claim 15 wherein at least a portion of the oligonucleotide subunits are linked via a multifunctional moiety derived from a compound of the formula:

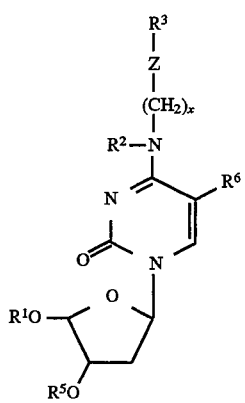

where Z is a nucleophile, $R^1$ is a protective group that is generally base-stable and acid sensitive, $R^2$ is hydrogen or methyl, $R^3$ is a protective group that can be removed and replaced with hydrogen without affecting $R^1$, $R^5$ is a phosphorus derivative that enables addition of nucleotides to the 5' position of an oligonucleotide chain during chemical synthesis, $R^6$ is methyl, hydrogen, I, Br, or F, and X is an integer in the range of 1 to 8, inclusive.

26. The probe of claim 15 wherein at least a portion of the oligonucleotide subunits are linked via a multifunctional moiety derived from a compound of the formula:

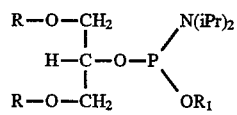

where R is a hydroxyl protecting group, iPr is isopropyl, and $R^1$ is methyl or betacyanoethyl.

27. The probe of claim 15 in which the second domain (M) has at least one covalent branch point comprising a cytosine base which has been modified at the $N^4$ position, wherein each of said modified cytosine bases has at least one of said single-stranded oligonucleotide subunits covalently bonded directly or indirectly via said $N^4$ position.

28. A molecular probe for use as a signal amplifier in immunoassays comprising:

(a) a first domain (A) comprising a polypeptide capable of functioning as an antibody which binds specifically to a known analyte; and (b) a second domain (M) comprising a multiplicity of single-stranded oligonucleotide subunits that are capable of hybridizing specifically to a single-stranded nucleic acid of interest, wherein said multiplicity of subunits comprises at least two identical subunits, wherein said second domain (M) consists of a branched polynucleotide having a minimum of three termini, which are of the 3' or 5' type, and at least one covalent branch point, wherein the multiplicity of single-stranded oligonucleotide subunits are bonded directly or indirectly only via covalent bonds and wherein said first domain is covalently conjugated to said second domain.

29. The probe of claim 28 in which the second domain (M) has at least one covalent branch point comprising a cytosine base which has been modified at the $N^4$ position, wherein each of said modified cytosine bases has at least one of said single-stranded oligonucleotide subunits covalently bonded directly or indirectly via said $N^4$ position.

30. A molecular probe for use as a signal amplifier in immunoassays comprising:

(a) a first domain (A) comprising a polypeptide capable of functioning as an antibody which binds specifically to a known analyte; and (b) a second domain (M) comprising a multiplicity of single-stranded DNA oligonucleotide subunits that are capable of hybridizing specifically to a single-stranded nucleic acid of interest, wherein said second domain (M) consists of a branched polynucleotide having a minimum of three termini, which are of the 3' or 5' type, and at least one covalent branch point, wherein the multiplicity of single-stranded oligonucleotide subunits are bonded directly or indirectly only via covalent bonds and wherein said first domain is covalently conjugated to said second domain.

31. The probe of claim 30 in which the second domain (M) has at least one covalent branch point comprising a cytosine base which has been modified at the $N^4$ position, wherein each of said modified cytosine bases has at least one of said single-stranded oligonucleotide subunits covalently bonded directly or indirectly via said $N^4$ position.

* * * * *